United States Patent [19]

Pendery

[11] Patent Number: 4,490,564
[45] Date of Patent: Dec. 25, 1984

[54] MIXED SOLVENT RECOVERY OF 4,4'-DIHYDROXYBIPHENYL

[75] Inventor: John J. Pendery, Huntington Woods, Mich.

[73] Assignee: Ethyl Corporation, Richmond, Va.

[21] Appl. No.: 487,856

[22] Filed: Apr. 22, 1983

[51] Int. Cl.³ .................... C07C 37/02; C07C 39/12
[52] U.S. Cl. .................................................. 568/730
[58] Field of Search ........................................ 568/730

[56] References Cited

U.S. PATENT DOCUMENTS 4,340,768 7/1982 Jinbo .................................. 568/730

FOREIGN PATENT DOCUMENTS 1930341 12/1970 Fed. Rep. of Germany ...... 568/730
0022347 2/1979 Japan .................................. 568/730

Primary Examiner—Werren B. Lone
Attorney, Agent, or Firm—Donald L. Johnson; John F. Sieberth; Teresa M. Stanek

[57] ABSTRACT

A process for the preparation of 4,4'-dihydroxybiphenyl having high purity by hydrolyzing 4,4'-dibromobiphenyl in the presence of a hydrolysis catalyst in an alkaline aqueous solution, separating the catalyst from the alkaline aqueous solution, acidifying the alkaline aqueous solution with an acid to form crude solid 4,4'-dihydroxybiphenyl, separating the 4,4'-dihydroxybiphenyl, dissolving the 4,4'-dihydroxybiphenyl in an inert organic solvent which is preferably at an elevated temperature, adding water to the inert organic solvent mixture which allows the inorganic salt that may be present to remain in solution and the 4,4'-dihydroxybiphenyl begins to precipitate out of solution and recovering the precipitated solid 4,4'-dihydroxybiphenyl having high purity.

8 Claims, No Drawings

MIXED SOLVENT RECOVERY OF 4,4'-DIHYDROXYBIPHENYL

BACKGROUND OF THE INVENTION

1. Field of the Invention

The present invention is directed to the preparation of 4,4'-dihydroxybiphenyl. More particularly, this invention involves the hydrolysis of 4,4'-dibromobiphenyl in the presence of a copper compound catalyst. A mixed solvent system is used to recover pure 4,4'-dihydroxybiphenyl from the crude product.

2. Description of the Prior Art 4,4'-Dihydroxybiphenyl is useful as an antioxidant for a resin, an intermediate for a dye and a starting material for polyesters, polyepoxides, polyurethanes and polycarbonates. It may also be used as a co-monomer in high performance polyester film, cable, rope and engineering plastics.

U.S. Pat. No. 4,340,768 teaches the production of 4,4'-dihydroxybiphenyl by hydrolyzing 4,4'-dibromobiphenyl in the presence of a copper compound catalyst in an aqueous solution, extracting by-products from the alkaline aqueous solution with an alcohol or ketone which forms an organic phase, neutralizing or acidifying the alkaline aqueous solution with an acid, extracting the reaction product with the alcohol or ketone and finally crystallizing the reaction product from the extracted solution. This process requires two extractions using an alcohol or ketone. The first extraction is designed to remove by-product impurities.

Copending application U.S. Ser. No. 469,724, filed Feb. 25, 1983 describes a process for preparing 4,4'-dihydroxybiphenyl. However, a rather lengthy process is used to recover pure 4,4'-dihydroxybiphenyl from the crude product. After the acidification and separation to obtain the crude product, the solid crude product was then dissolved in an inert organic solvent leaving an inorganic salt residue. The salt residue was separated and removed. An aromatic hydrocarbon such as toluene may be added to this solution to azeotrope out residual water during the distillation to produce a dry product. Unfortunately, the quality of the product obtained in this manner was oftentimes quite crude and further recrystallization or purification was therefore necessary.

It has now been discovered that immediately after the acidification and separation to obtain a crude product, a relatively pure product can readily be obtained using water and an inert organic solvent in which the 4,4'-dihydroxybiphenyl (biphenol) is soluble.

SUMMARY OF THE INVENTION

According to the present invention, 4,4'-dihydroxybiphenyl having high purity can be prepared by hydrolyzing 4,4'-dibromobiphenyl in the presence of a hydrolysis catalyst in an alkaline aqueous solution, separating said catalyst from said alkaline aqueous solution, acidifying said alkaline aqueous solution with an acid, forming crude solid 4,4'-dihydroxybiphenyl, separating said 4,4'-dihydroxybiphenyl, dissolving said 4,4'-dihydroxybiphenyl in an inert organic solvent, adding water to said inert organic solvent mixture. The inorganic salt that may be present as a residue goes into solution and said 4,4'-dihydroxybiphenyl begins to precipitate out of solution and said precipitated solid 4,4'-dihydroxybiphenyl is recovered.

DESCRIPTION OF THE PREFERRED EMBODIMENTS

In accordance with the present invention, 4,4'-dihydroxybiphenyl having high purity can be prepared by hydrolyzing 4,4'-dibromobiphenyl in the presence of a hydrolysis catalyst in an alkaline aqueous solution. The pure product is obtained from the crude product using a double solvent recovery technique.

The reaction is carried out in an autoclave filled with either $N_2$ or air. Similar results are obtained in either system. However, preferred reaction times and temperatures are generally lower in an air environment.

Any typical hydrolysis catalyst may be used in the practice of the present invention. Typical hydrolysis catalysts include copper, nickel, silver and the like. A copper compound catalyst is preferred. The copper compound catalyst used in the practice of the present invention is preferably in the plus two oxidation state. Typical catalysts include a copper chelate, a cupric halide such as cupric bromide or cupric chloride, cupric acetate, cupric citrate, cupric sulfate, cupric tartrate, and the like. A desirable copper compound catalyst in the practice of the present invention is copper sulfate. The copper catalyst precipitates from solution after the hydrolysis reaction and is filtered out.

The amount of catalyst used in the practice of the present invention varies depending on the reaction conditions selected. The amount of catalyst should be sufficient to hydrolyze 4,4'-dibromobiphenyl to 4,4'-dihydroxybiphenyl. The amount of catalyst used is oftentimes within the range of about 0.1 to about 5.0 weight percent of the 4,4'-dibromobiphenyl charged. More preferably, the amount of catalyst is within the range of about 0.5 to about 2.0 weight percent of the 4,4'-dibromobiphenyl charged.

The hydrolysis initially occurs in an alkaline aqueous medium. Any alkali metal hydroxide can be used to obtain a suitable alkaline medium. Typical alkaline hydroxides include sodium hydroxide, lithium hydroxide, potassium hydroxide, and the like. The pH is greater than 7. The amount of base used is in stoichiometric excess of that required to neutralize the solution. Generally, the pH is within the range of about 9 to 14.

The hydrolysis generally begins at elevated temperature and the system is gradually heated up from room temperature to about 300° C. Oftentimes, the temperature is within the range of about 50° C. to about 300° C.

Reaction time varies depending on the conditions selected and the desired conversion. The reaction time generally ranges from 1 hour to 3 hours. Preferably, the reaction time ranges from 1 to 2 hours.

The alkaline aqueous solution containing the 4,4'-dihydroxybiphenyl product is then acidified with an acid. The pH of the solution is less than 7.0. Any type of acid may be used in the practice of the present invention. Typical acids include hydrochloric acid, hydrobromic acid, sulfuric acid, phosphoric acid, hydroiodic acid, acetic acid, and the like. The preferred acid is hydrobromic acid. The desired product precipitates out of solution and is filtered. The water content of the product may be decreased by pressing.

At this point the solid product is dissolved in an inert organic solvent in which the solid 4,4'-dihydroxybiphenyl is soluble. Generally, the inorganic salts which may be also present are either insoluble or slightly soluble in this inert organic solvent. The crude product contains inorganic salts such as sodium sulfate, sodium bromide and the like. This crude product may be added to the inert organic solvent, or the solvent may be added to the crude product. The solvent may be at room temperature or heated. The inert organic solvent may be heated prior to its addition to the crude biphenol or heat may be added after the addition. It is preferable for the solvent to be heated above room temperature since this increases the solubility of the crude biphenol in the solvent. It is more preferable for the solvent to be heated to its boiling point. The minimum amount of inert organic solvent is therefore necessary. The addition of inert organic solvent is stopped once essentially all of the crude product is in solution.

Typical inert organic solvents intended for use in the present invention include carboxylic acid esters, such as methyl acetate, ethyl acetate, amyl acetate, methyl propionate, ethyl propionate, methyl butyrate, methyl hexanoate, methyl heptanoate, methyl oleate, methyl linoleate, methyl stearate and other acid esters having three to eighteen carbon atoms, also ethers and cyclic ethers, such as diethyl ether, tetrahydrofuran, dioxane, and the like, poly(ethylene glycol) ethers, such as ethylene glycol monomethyl ether, ethylene glycol dimethyl ether, diethylene glycol monomethyl ether, diethylene glycol dimethyl ether, triethylene glycol monoethyl ether, triethylene glycol dimethyl ether, polyethylene glycol monoethyl ether, polyethylene glycol dimethyl ether, and the like.

The preferred organic solvent is an alcohol or a ketone. Suitable alcohols include methanol, ethanol, propanol, ispropanol, 1-butanol, 2-butanol, isobutanol, 1-pentanol, 2-pentanol, 1-hexanol, 1-heptanol, 2-heptanol, 1-octanol, 2-ethyl-1-hexanol, cyclohexanol, cyclopentanol, n-amyl alcohol, isoamyl alcohol, t-amyl alcohol, neopentyl alcohol, capryl alcohol, n-decyl alcohol, ethylene glycol, 1,2-propanediol (dl), 1,3-propanediol, 1,3-butanediol (dl), 1,4-butanediol, 2,3-butanediol (mixt.), 1,5-pentanediol, glycerol, and the like.

Suitable ketones include acetone, 2-hexanone, 3-hexanone, methyl isobutyl ketone, 2-heptanone, 4-heptanone, diisobutyl ketone, mesityl oxide, phorone, isophorone, cyclohexanone, acetophenone, methyl cyclohexanone, methyl ethyl ketone, methyl n-propyl ketone, diethyl ketone, methyl t-butyl ketone, diisopropyl ketone, di-n-amyl ketone, and the like. The more preferred organic solvents are acetone are isopropanol.

Preferably, the inert organic solvent mixture is at an elevated temperature. This allows for increased solubility of the 4,4'-dihydroxybiphenyl (biphenol) in the solvent. More preferably, the inert organic solvent mixture is heated to reflux. Water is then added to the inert organic solvent mixture. The amount of water added is sufficient to allow the inorganic salt that may be present to remain in solution. In some cases, a majority of the inorganic salt does not go into solution until the water is added. The water may be at room temperature since it will be heated to the temperature of the already boiling mixture. Eventually, all the inorganic salt residue is in solution and the 4,4'-dihydroxybiphenyl beings to precipitate out of solution. The inert organic solvent mixture is then allowed to cool causing the remainder of the 4,4'-dihydroxybiphenyl to precipitate out of solution. The pure 4,4'-dihydroxybiphenyl product is recovered usually by filtration and allowed to air dry.

The present invention is further illustrated by the following example which is provided for purposes of illustration and is not intended to limit the present invention.

EXAMPLE 1

Preparation of Crude Biphenol

A 600 ml autoclave was charged with 400 ml of 1N NaOH (0.4 mole), 11.5 g (37 mmole) 4,4'-dibromobiphenyl and 64 mg (0.256 mmole) $CuSO_4.5H_2O$ as 4 ml of 0.064M solution in $H_2O$. The autoclave was pressure checked with $N_2$ to 1100 psi, vented, flushed with air and resealed. The autoclave was heated to 300° C. at an autogenic pressure of 1168 psi. These conditions were maintained for two hours. After cooling and venting the aqueous reaction product was filtered to remove a grey solid which probably contained catalyst and unreacted starting material. This filter was then removed to a second filter flask. Any starting material remaining was recovered by washing with acetone and stripping the solvent on a rotary evaporator. The filtered aqueous product solution was acidified (pH2) with 25% sulfuric acid. The precipitated crude biphenol (4,4'-dihydroxybiphenyl) was filtered and washed with water (50 ml).

EXAMPLE 2

Recrystallization from Methanol/Water

Crude biphenol (15.0 g) prepared similar to that described in Example 1 was dissolved in boiling methanol (73.63 g; 93.0 ml). The solution was maintained at a gentle boil while distilled deionized water (8.45 g; 8.5 ml) was added in small portions until the solution became slightly cloudy. The solution was allowed to cool slowly to room temperature over several hours. The solid was filtered and washed with water.

Table 1 compares the recrystallized biphenol from Example 2 with crude biphenol. A 92.5% purity of biphenol resulted after the purification procedure compared to 82.0% biphenol in the curde material. The percent of absolute recovery was calculated from the weight charged and the weight recovered. The recovery of biphenol can be obtained by dividing the absolute recovery by 82% (the biphenol content of the composite). The biphenol purity in Table 1 was determined by VPC weight percent analysis.

EXAMPLE 3

Recrystallization from Iso-Propanol/Water

This example followed the same procedure as Example 2 except that the crude biphenol (15.0 g) was dissolved in boiling iso-propanol (73.9 g; 94.1 ml). 81.9 g of water was added. The recrystallized product was 95.8% biphenol.

EXAMPLE 4

Recrystallization from Acetone/Water

This example followed the same procedure as Example 2 except that the crude biphenol (15.0 g) was dissolved in boiling acetone (60.0 g; 76 ml). 51.9 g of water was added. The recrystallized product was 96.3% biphenol.

TABLE 1

Purification of Biphenol Using a Mixed Solvent Recovery System

| Sample | Solvent | Absolute Recovery (Percent) | Melting Point (°C.) | Biphenol (VPC wt. %) |
|---|---|---|---|---|
| Crude Material | none | — | 262–273 | 82.0 |
| Example 2 | Methanol/water | 62.8 | 273–279 | 92.5 |

TABLE 1-continued

Purification of Biphenol Using a Mixed Solvent Recovery System

| Sample | Solvent | Absolute Recovery (Percent) | Melting Point (°C.) | Biphenol (VPC wt. %) |
|---|---|---|---|---|
| Example 3 | Isopropanol/Water | 63.7 | 278–281 | 95.8 |
| Example 4 | Acetone/Water | 46.0 | 277–282 | 96.3 |

Table 1 demonstrates the improved purity that is obtained by recrystallizing crude biphenol in several mixed solvent systems.

I claim:

1. A process for the preparation of 4,4'-dihydroxybiphenyl having high purity, said process comprising:
    (a) hydrolyzing 4,4'-dibromobiphenyl in the presence of a copper compound hydrolysis catalyst in an alkaline aqueous solution and at a temperature of from room temperature to about 300° C.;
    (b) separating said catalyst from said alkaline aqueous solution;
    (c) acidifying said alkaline aqueous solution with an acid, forming crude solid 4,4'-dihydroxybiphenyl;
    (d) separating said 4,4'-dihydroxybiphenyl;
    (e) dissolving said 4,4'-dihydroxybiphenyl in an inert organic solvent;
    (f) adding water to said inert organic solvent which allows the inorganic salt that may be present to remain in solution and said 4,4'-dihydroxybiphenyl begins to precipitate out of solution; and
    (g) recovering said precipitated solid 4,4'-dihydroxybiphenyl.

2. A process, as recited in claim 1, wherein said inert organic solvent is at an elevated temperature and said inert organic solvent system is cooled once said 4,4'-dihydroxybiphenyl begins to precipitate out of said solution after the addition of said water.

3. A process, as recited in claim 2, wherein said inert organic solvent is heated to reflux.

4. A process, as recited in claim 3, wherein said inert organic solvent is an alcohol or ketone.

5. A process, as recited in claim 4, wherein the hydrolysis temperature ranges from 50° C. to about 300° C.

6. A process, as recited in claim 5, wherein said catalyst is about 0.1 to about 5.0 weight percent of the 4,4'-dibromobiphenyl charged.

7. A process, as recited in claim 6, wherein said copper compound catalyst is cupric sulfate.

8. A process, as recited in claim 7, wherein said acid is hydrobromic acid.

* * * * *